United States Patent [19]

Gottlieb

[11] Patent Number: 4,616,079

[45] Date of Patent: Oct. 7, 1986

[54] IMMUNOAMPLIFIERS AND PROCESSES FOR THE EXTRACTION THEREOF

[75] Inventor: A. Arthur Gottlieb, New Orleans, La.

[73] Assignee: Imreg, Inc., New Orleans, La.

[21] Appl. No.: 643,724

[22] Filed: Aug. 24, 1984

[51] Int. Cl.[4] .......................... C07K 1/14; C07K 15/06; A61K 35/14

[52] U.S. Cl. ..................................... 530/344; 530/417; 530/380; 530/829; 424/85; 424/88; 424/92; 424/101; 514/21

[58] Field of Search ....................... 260/112 R, 172 B; 424/85, 88, 92, 101; 514/21

[56] References Cited

U.S. PATENT DOCUMENTS

| | | | |
|---|---|---|---|
| 3,991,182 | 11/1976 | Spitler et al. | 424/101 |
| 4,132,776 | 1/1979 | Jeter | 424/101 |
| 4,435,384 | 3/1984 | Warren | 424/101 |
| 4,468,379 | 8/1984 | Gottlieb | 424/101 |

OTHER PUBLICATIONS

Wotila, Transfer Factor & Other Immunological Activities of Human Leucocyte Dialysate and Other Dialysates of Mammalian Tissues (1979), pp. 2-4, 6-7, 12-17, 22-23 and 25-27.

*Primary Examiner*—Howard E. Schain
*Attorney, Agent, or Firm*—Richard H. Stern

[57] ABSTRACT

A high pressure liquid chromatography process is described for the extraction of materials that nonspecifically amplify the immune response to antigens to which the subject was previously or is concomitantly exposed. The materials are also described, as are methods and compositions for the use thereof in connection with hypoimmune conditions.

18 Claims, 8 Drawing Figures

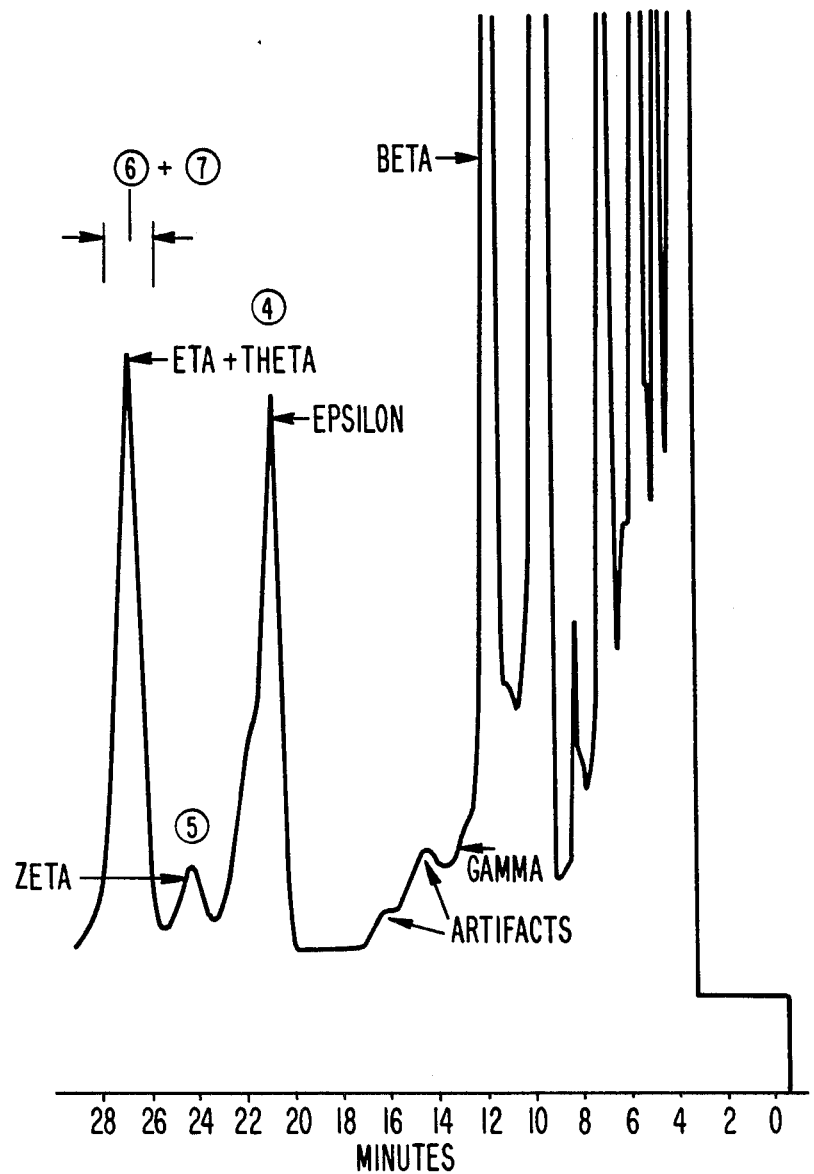

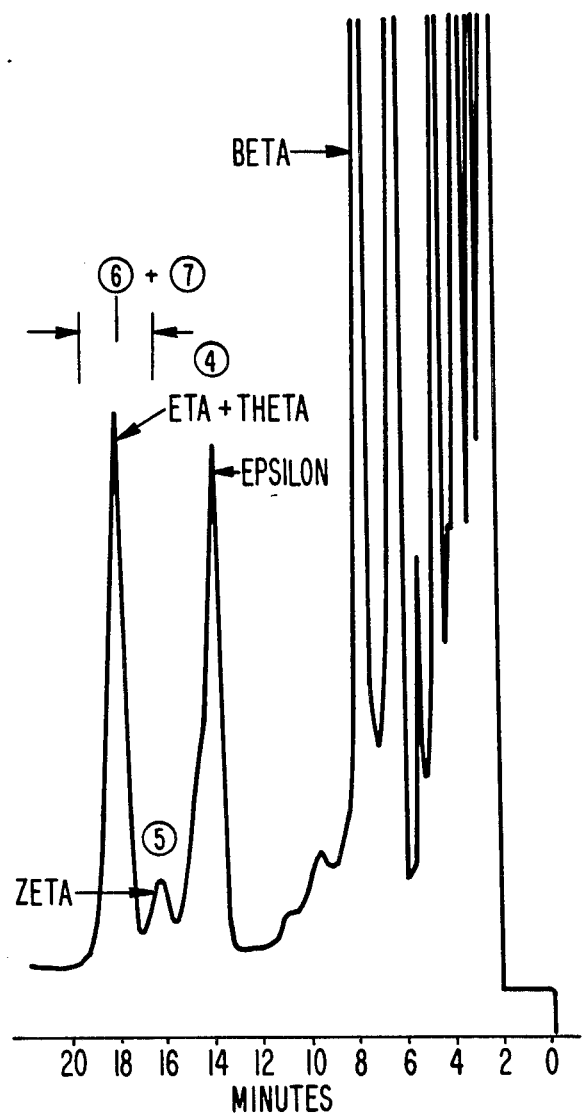

IMMUNOAMPLIFIERS AND PROCESSES FOR THE EXTRACTION THEREOF

BACKGROUND OF THE INVENTION

1. Field of Invention

The human immune system, although highly complex and at present imperfectly understood, is presently considered to have two principal aspects: (1) humoral immunity, which is mediated by circulating antibodies; and (2) cell-mediated immunity which is mediated by lymphoid cells. Humoral immunity can be transferred from an immune donor to a non-immune recipient by means of serum immunoglobulins. Such serum-mediated transfers result in immune responses that are manifest almost instantly. Cell-mediated immunity can be transferred by means of peripheral blood leukocytes, or preparations thereof; such immune responses develop over a period of several hours. The present invention concerns cell-mediated immunity.

A typical manifestation of cell-mediated immunity is the delayed hypersensitivity ("DH") skin reaction. A DH skin reaction is observed when the appropriate antigen is injected subcutaneously. Within 24 to 48 hours, local inflammation (erythema) and a swelling and thickening (induration) are observed in a sensitive individual. The degree of sensitivity may be measured by the size and severity of the reaction. The DH reaction also presents characteristic histological findings—specifically, perivascular infiltration of lymphocytes and monocytes in the inflamed area. The cells seen at the site of a DH reaction are derived from the peripheral blood leukocyte population.

The mechanisms of cell-mediated immunity are as yet incompletely understood. It is known that the cells which mediate the response are capable of responding in a variety of ways to a challenge from an antigen. These responses include: proliferation of cells bearing specific sensitivity to a given antigen; the induction and multiplication of cells mediating a variety of immune functions, including antibody production; and reactions against foreign cells and tumors.

The present invention relates to the discovery of (1) methods for extracting "amplifiers" of the immunity system, which are isolated from dialyzed extracts of leukocytes, and (2) the amplifiers themselves that are so extracted. These amplifiers profoundly affect the quality and quantity of cell-mediated immunity responses; are useful in the treatment of a variety of clinical conditions characterized by inadequate reaction to a specific antigen; and are useful in the alleviation of certain anergic conditions.

Much of the background relevant to the instant application is found in the specification of copending application Ser. No. 441,432, which is presently scheduled to issue as U.S. Pat. No. 4,468,379, on Aug. 28, 1984. That application (hereinafter referred to at times as "the cited copending application") is a continuing application based on then copending application Ser. No. 256,886, filed May 6, 1982, which was a continuing application based on then copending Ser. No. 149,737, filed May 14, 1980.

2. Prior Art

The prior art in this field is discussed in the cited copending application, and that discussion is incorporated herein by reference.

Transfer factor. Much of the prior art concerns the so-called "transfer factor," a product very different from the subject matter of this invention and in some ways antithetical in concept thereto. When a "transfer factor" preparation is made from leukocytes of a donor known to be sensitive to a given antigen, and the preparation is injected subcutaneously into the skin of a recipient known to be insensitive to the given antigen, and subsequently the recipient is challenged with the given antigen—a DH response is observed. Normally, the recipient, in the absence of the injected "transfer factor" preparation, would have been unresponsive to the challenge from the given antigen.

The "transfer factor" phenomenon is believed by the inventor to be demonstrable in human beings only with regard to substances derived from human beings (although some researchers have claimed to derive from animals "transfer factors" that could be used in human beings). Progress in fractionating and characterizing "transfer factor" has been impeded by the lack of associated structural or chemical criteria and by the fact that the phenomena observed after fractionation are often qualitatively different from the phenomena induced by the original dialysate. Although the term "transfer factor" appears in literature as applied to fractionated preparations, and as monitored by criteria other than a DH skin response, it is unclear whether in such terminology the term "transfer factor" is indeed used to refer to a single biochemical entity or to an activity that represents a single biological function, or rather to refer to a mixture of materials of various kinds. Such dialysates may, and the inventor believes that they typically do, contain various different molecules and entities.

Some of the work in this field was summarized and commented on by A. Uotila, in *Transfer Factor and Other Immunological Activities of Human Leukocyte Dialysate and Other Dialysates of Mammalian Tissues* (1979). Uotila's monograph indicates that preparations of so-called "transfer factor" may contain a large variety of substances. Uotila suggested that an "augmenting activity" can be derived from dialyzable leukocyte extracts in guinea pigs, but did not disclose whether this is one or several different materials or activities, or if the latter, how to separate them from one another. As explained in the specification of the cited copending application, the inventor believes that this monograph is of interest primarily because it teaches away from the disclosure of the copending, and also the instant, patent application.

Comparison of Transfer Factor and Modulators of Cited Copending Application

Modulators. The cited copending application and also the instant invention relate to what the inventor terms "modulators" of the human or animal immune system. A "modulatornn" as therein and herein defined is, in general terms, any substance or material that has a "modulator activity."

To have a modulator activity is to affect a response, whether direct or indirect, of an animal or human body, portion thereof, or matter taken therefrom, to the reintroduction of antigens to which said body has been previously exposed, where such response is specifically attributable to the function of the immunity system of said animal or human.

Substances having general bodily effects that may also include effects on the immune response are not subsumed within the term "modulator," as herein defined. Such modulators manifest their activity in a DH skin reaction test, and therefore appear to exert their primary effect on the cell-mediated immunity system. It will be understood, however, that such modulators have broad effects on the entire immunity system, and may also affect the humoral immunity system.

Amplifiers. An amplifier is a modulator that amplifies the onset, or rate or intensity, of the immune response. Hence, it may be said that "amplifier" material is that modulator material characterized, in general terms, by "amplifier" activity, i.e., the production of a greater than normal immune response (faster or stronger, or both) in a sensitive recipient, following injection of an antigen to which the recipient is already sensitive. The instant application primarily concerns amplifiers, also termed at times "immunoamplifiers," and methods of extraction thereof.

The term "amplifier" is used, at times herein to refer to both genus and species. That is, "amplifier material" may be a mixture of amplifier species. It may also contain extraneous material, which is without amplifier activity. Moreover, it is by no means suggested that any single amplifier species extracted by the methods of the invention is a single molecular species rather than a mixture of molecules. Amplifier material is considered useful in the treatment of anergic conditions and conditions of immune deficiency, both local and systemic, as in the Acquired Immune Deficiency ("AIDS") Syndrome and related conditions.

It will be understood that "transfer factors" are not amplifiers, as defined above, since the effect of a transfer factor is observed in a recipient who has not previously been exposed to a given antigen, while the effect of an amplifier is observed only upon or following reintroduction of an antigen to which the recipient was previously exposed. Furthermore, transfer factor effects are specific with respect to a given antigen, but amplifiers exert non-specific effects with respect to any antigen to which the recipient was previously exposed.

SUMMARY OF THE PRESENT INVENTION

In the cited copending application, eight specific modulators of the human immune system were described that have been isolated from dialysates of leukocyte extracts. Six such modulators described therein have amplifier activity and two have suppressor activity. These six amplifiers were designated amplifiers 1-6. These two suppressors were identified as the S-suppressor and the L-suppressor. Processes for the extraction of these modulators are described in the cited copending application. The processes are based on high-pressure reverse-phase liquid chromatography, using an ethanol-in-water gradient and octadecylsilane as the basic chromatography system. Various amplifiers elute at specified parts of the ethanol-in-water gradient, and can be indentified in terms of the ethanol concentration of the material ("effluent") coming off the chromatography column.

The instant invention is in the nature of an improvement on the subject matter of the cited copending application. The inventor has discovered additional processes for the extraction of amplifiers, and has discovered amplifier materials that can be extracted from leukocyte preparations by such processes. The chromatography system of the instant invention uses acetonitrile-phosphate aqueous gradients, rather than ethanol in water, and permits the isolation of approximately four to seven amplifier materials. The principal benefit of the newly discovered processes is the elimination of the need for some of the steps of the original process and the easier and perhaps more effective extraction processes now provided, which allow a much more econbmical manufacture of amplifiers and much greater volume of production.

DESCRIPTION OF THE DRAWINGS

FIGS. 1A, 1B, and 1C are similar graphs for other runs of the process.

DETAILED DESCRIPTION OF THE PREFERRED EMBODIMENT

Figure 1:
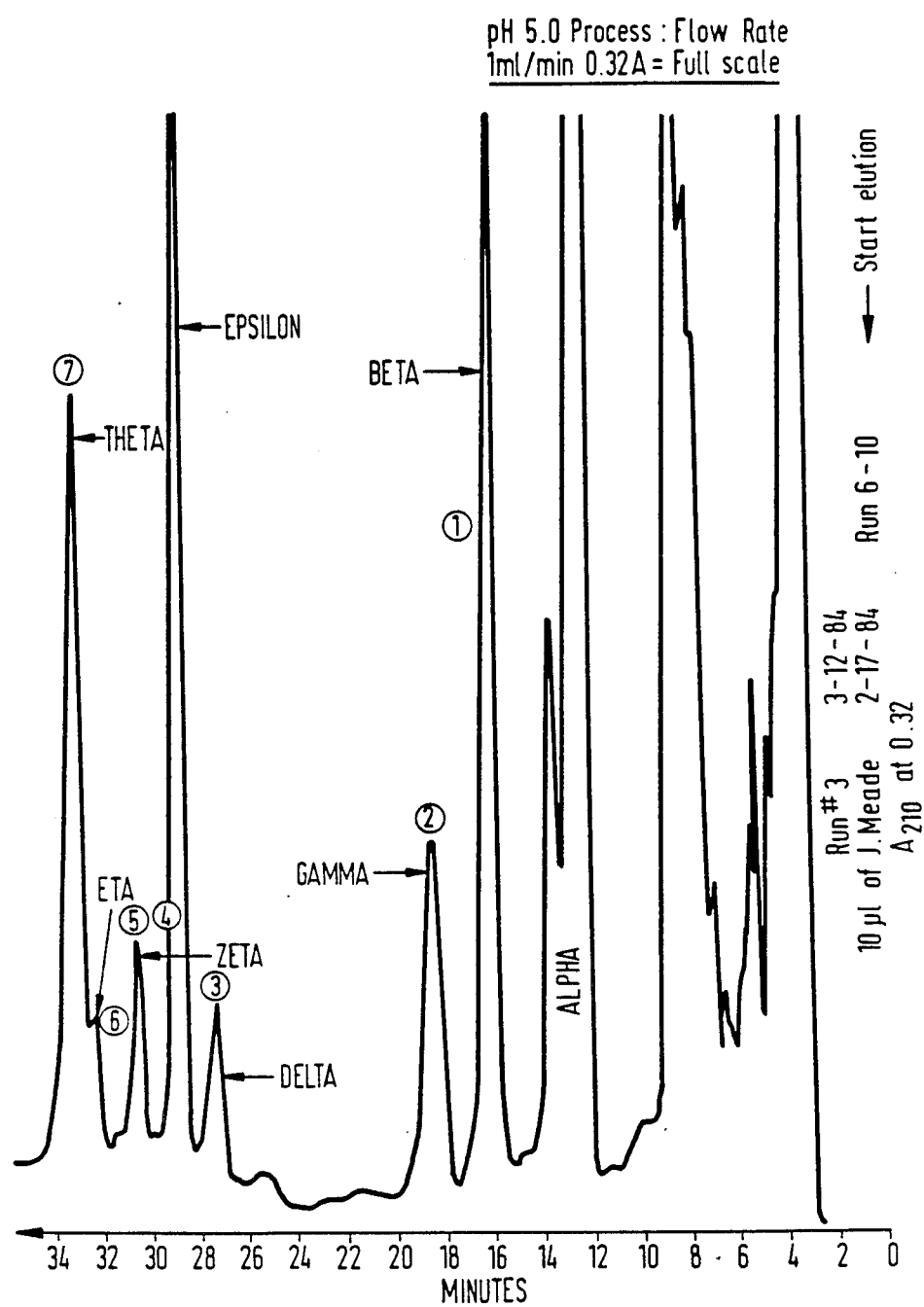
FIG. 1 is a graph of 210 nm ultraviolet absorption of the effluent as it elutes from the HPLC column in the pH 5 extraction process of Example 4. The vertical axis represents absorbance units (full scale=0.32 units), and the horizontal axis represents time (2 minutes/division). The fractions of effluent material are identified by name (Greek letters).

In the following discussion, procedures are described wherein materials were obtained from human donors and test measurements were made on human recipients. The procedures and reagents used herein were chosen to provide sterile and non-toxic products for human treatment. Despite the toxicity of acetonitrile, the end products of the processes are nontoxic and they are free of acetonitrile.

The initial step in the preparation of the modulator material of this invention is preparation of leukocyte pellets, followed by separation of the small M.W. (under 3500) fractions of leukocyte extract of interest herein.

EXAMPLE 1

Preparation and Filtration of Leukocyte Extracts

Leukocyte pellets were prepared by the methods of Example 1 of the cited copending application. The "S" (or "small" M.W.) fraction of the extract is isolated by the ultrafiltration method of Example 3 of the cited copending application. (Note: Dialysis in accordance with Example 2 of the cited copending application is an equivalent process.)

The next step in the preparation is gel filtration of the S fraction, to partially purify the material of interest from other material, and to separate the S-fraction material into a number of separate fractions having different characteristics. The following two procedures of the cited copending application (Examples 2 and 3) have been found unnecessary to carry out the pH 5 process of Example 4 of this application. It has not been verified, however, that they can be omitted with impunity in the pH 2.5 process of Example 6 of this application.

EXAMPLE 2

Gel Filtration

Gel filtration is carried out on the leukocyte extract of preceding Example 1, in accordance with the method of Example 4 of the cited copending application. The resulting fractions were collected and set aside. (Note:

Gel exclusion chromatography is described in the cited copending application as an equivalent of gel filtration.)

EXAMPLE 3

Assay of Fractions

The fractions of preceding Example 2 are assayed in accordance with the procedure of the cited copending application. The major and secondary fluorescamine-reactive ("fluram-reactive") peaks were detected and those fractions were selected and set aside for further purification, described below.

Reverse Phase Liquid Chromatography

Further purification of the material of preceding Examples 1 to 3 was carried out by two different reverse-phase high pressure liquid chromatography ("HPLC") processes (referred to hereinafter at times as the pH 5 process and the pH 2.5 process) discovered by the inventor.

The first process (the pH 5 process) may be used with either the material of preceding Examples 1, 2, or 3. The second process (the pH 2.5 process) may be used with the material of preceding Example 3, and it is not known whether effective results can be obtained by starting with the material of Example 1 or 2. Each process uses an octadecylsilane ("O.S.") resin column eluted with a gradient of acetonitrile in aqueous phosphate solution. (All percentage references to gradients hereinafter are on a v/v basis.) The acetonitrile is HPLC grade (J. T. Baker Co., Phillipsburg, N.J.). The O.S. is a Waters Associates (Milford, Mass.) "mu Bondapak" C18 Octadecyl Silane reverse-phase analytical column (0.39 cm (ID)×30 cm). The apparatus is a Series 3B Perkin-Elmer dual-pump, high-pressure, liquid chromatograph. The Perkin-Elmer machine includes an ultraviolet absorbance detector, which scans the column output at absorption 210 nm.

The Perkin-Elmer Series 3B High Pressure Liquid Chromatograph can be programmed to operate at a specified flow rate, such as 1.0 ml/min, the rate that was used herein. Samples can then be collected at 1.0 minute intervals. A 0% to 20% solvent gradient can be programmed to run, for example, from 0% to 20% in 20 minutes. This divides the gradient into 20 1-minute intervals, during each of which intervals a 1.0 ml sample may be collected. Each such 1.0 ml sample should, in principle, represent a 1% change in solvent concentration. The visual display of the Perkin-Elmer machine shows the solvent concentration going into the column in accordance with the foregoing data.

As explained in the cited copending application, however, the actual solvent concentration in the effluent from the column (as measured, for example, by refractive indices of effluent calibrated against a standard curve) appears, in the earlier portions of the gradient, to be substantially less than the concentration of solvent being programmed (at that moment) into the column of the machine. This results from a variety of factors, such as size of the particular column, internal volume of the column, and the volume of tubes and connections leading into and out of the column. There may also be a time lag in lower concentration solvent being replaced with higher concentration solvent in the resin.

It is possible to calibrate these columns, and important to do so in order to facilitate repeatable results, because the solvent concentration coming out of the column (rather than going in) is the operative factor. The former, not the latter, is an invariant. This calibration can be done, with quite some difficulty in the case of solvents with a high vapor pressure (such as acetonitrile), by measurement of the effluent's refractive index and calculating actual solvent concentration therefrom. Furthermore, it is then possible to calibrate actual percentage solvent concentration against elution time for different flow rates, to facilitate the extraction procedure. If % concentration is the Y-axis and elution time (or tube number) is the X-axis, a series of approximately S-shaped calibration curves can be plotted for different throughput rates. It is also possible to estimate or calculate output solvent concentration from input solvent concentration data by various other means such as use of radioactive or fluorescent tracers, and in that manner develop a calibration curve.

It is believed that better results are realized by using some absolute measure of concentration of solvent, rather than elution time or tube number, as a measure of actual solvent concentration, the latter being the factor directly related to the solubility and chemical structure of the materials of interest. Accordingly, refractive index data are used hereinafter to identify the amplifiers described in this specification and in the claims thereof, where such data is available. In referring to gradient composition, however, it was deemed more appropriate at times to describe the separation process in terms of v/v percentage composition, because that is the basis on which acetonitrile and water are mixed to form the gradient. Also, it should be noted that for any constant system, where all other parameters remain constant, it is possible to use elution time as a measure or index, because there will be a regular correlation.

Figure 1A:
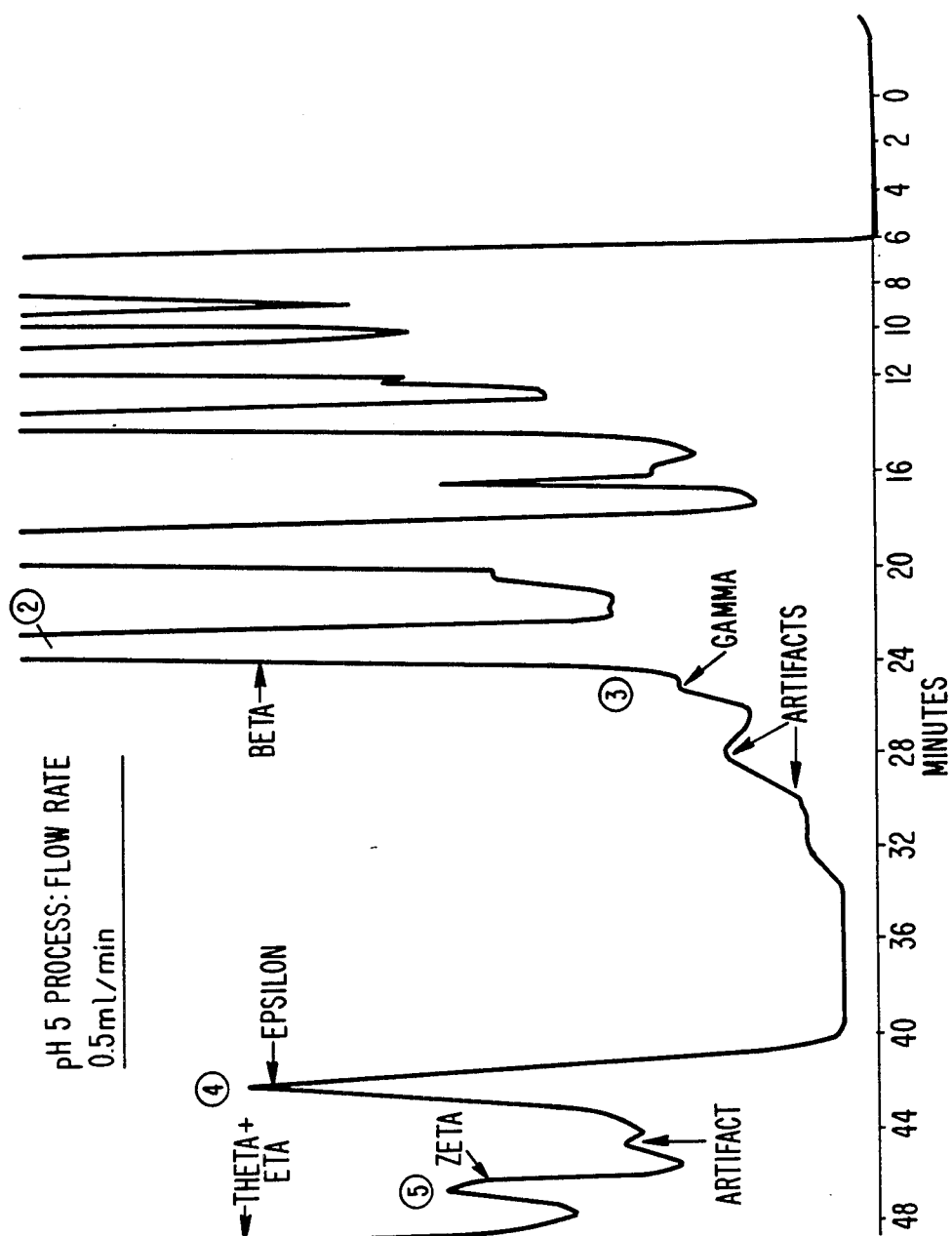
Figure 2:
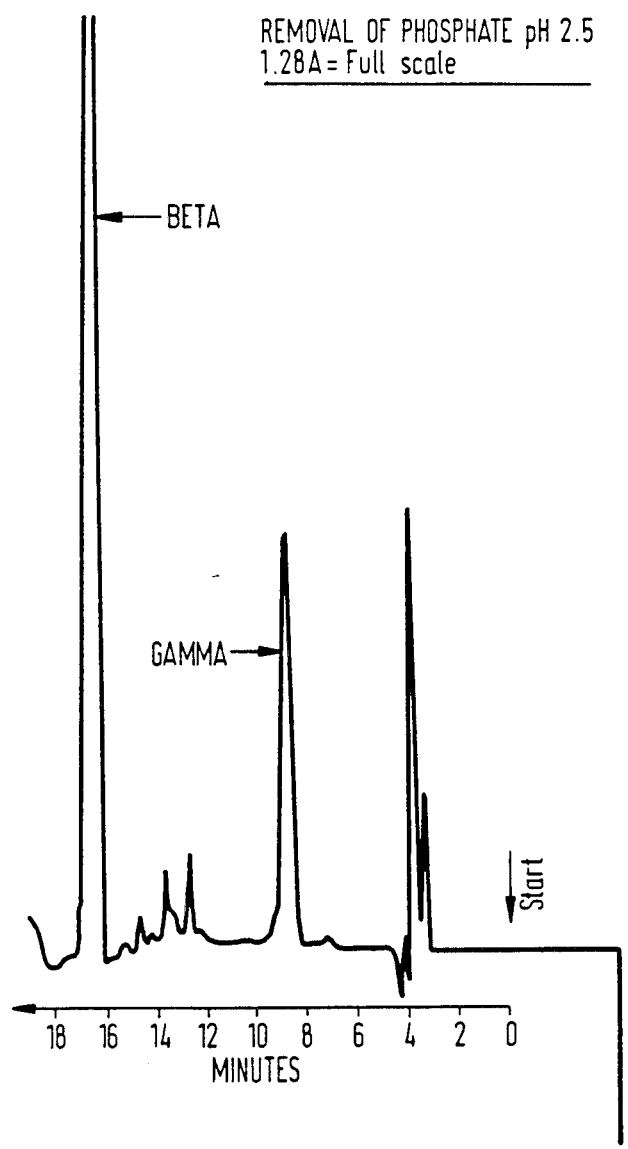
FIG. 2 is a similar graph for the purification process of Example 5, on Material Beta.
Figure 3:
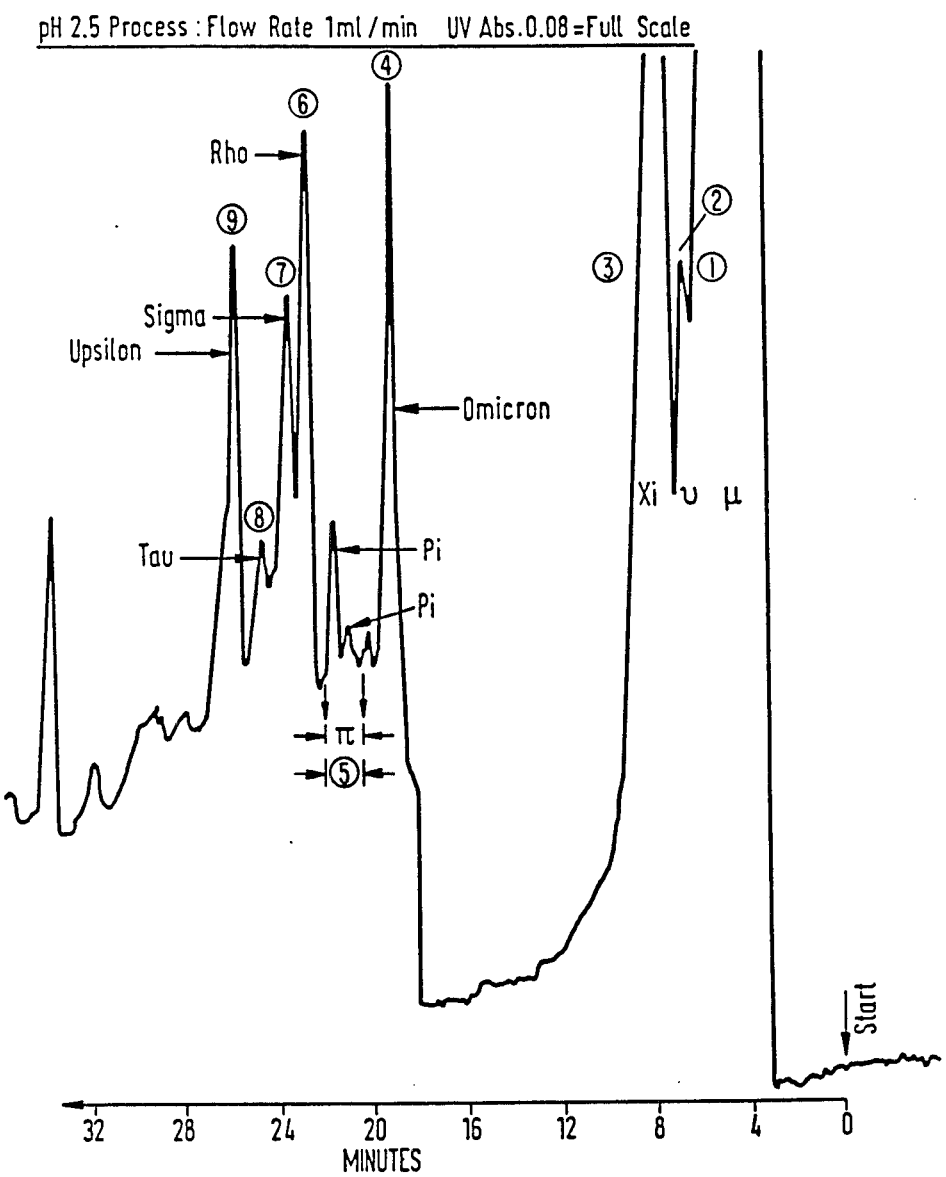
FIG. 3 is a similar graph for the pH 2.5 extraction process of Example 6.

An alternative absolute measure of the identity of the effluents is provided by the ultraviolet absorption profile characteristics of the range of effluents. It has been found that the shape of the ultraviolet absorption profile remains recognizable, despite some variations in the extraction procedure, such as a change in throughput rate. Accordingly, it is possible to identify particular materials as they come off the column by the shape of the absorption profile at that point. FIG. 1 shows such an ultraviolet absorption profile for the effluents of the pH 5 process. (FIGS. 2 and 3 show similar data for other processes described herein.) In FIGS. 1A, 1B, and 1C, the same preparation (a different one from that of FIG. 1) is run at flow rates of 0.5, 1.0, and 1.5 ml/min. It is seen that the profile remains recognizable, and also that it resembles that of FIG. 1.

In monitoring ultraviolet absorption, it is advantageous simultaneously to monitor "retention time" and also the machine's visual display of the solvent concentration at the column input. As indicated above, the display figures for concentration can by calculation be converted into estimated actual concentration data. "Retention time" is a measure of elution time. "Retention time" is used hereinafter to mean the time elapsed from the beginning of an HPLC run to the time that a particular effluent fraction passes the machine's ultraviolet detector unit on the way to the output. This occurs about 48 seconds before the effluent actually passes out of the column, because the volume of tubing between the detector and the output is approximately 0.8 ml and the flow rate is approximately 1 ml/min.

A description of the first acetonitrile purification process (the pH 5 process) follows. It may be used with the preparation of any of examples 1 to 3, and there is a clear economic advantage in using the less labor-intensive preparation of Example 1.

EXAMPLE 4

HPLC on Analytic Column, pH 5 Process

Material prepared in accordance with preceding Example 1 was further purified and separated by HPLC on the analytic column, as follows: First, an aqueous potassium phosphate solution was prepared (presumably, a mixture of $K_2HPO_4$ and $KH_2PO_4$) by adding 5M KOH aqueous solution dropwise to 0.02M reagent grade phosphoric acid aqueous solution until the pH of the solution was adjusted to pH 5.0. The solution was delivered to the Perkin-Elmer machine, along with HPLC grade acetonitrile. The machine was programmed to deliver the following three gradients: (1) 10 minutes of 0.1% concentration of acetonitrile in phosphate solution, constant gradient; (2) 45 minutes of 0.1% to 10.0%, linear gradient; and (3) 10 minutes of 10.0% to 15.0%, linear gradient. The flow rate was set at 1 ml/min. Then, 5–10 mg of material of preceding Example 1 was loaded into a "mu Bondapak" O.S. column, and HPLC was commenced.

As effluent was collected, the ultraviolet absorption of the effluent was scanned with the machine's ultraviolet detector (full scale=0.32 units). A plot of the absorption data is shown in FIG. 1. Apparent solvent concentrations, retention times, and ultraviolet absorption were recorded. The results of the run are explained below and summarized in Table A thereafter.

Materials extracted by the procedure (hereinafter identified by the names Materials Beta, Delta, Zeta, and Eta) have been tested by the modulator assay methods described in the cited copending application, and have been found to display amplifier activity. For that reason, these effluent fractions are collected and set aside, and the others (hereinafter identified by the names Alpha, Gamma, Epsilon, and Theta) are discarded.

As indicated, during the elution process, the ultraviolet absorption of the effluent was scanned at 210 nm, with full scale absorbance set at 0.32 units. As shown in FIG. 1, a distinct doublet ultraviolet absorption peak was observed at retention time 12–14 minutes (approximately 0.5 to 0.9% acetonitrile concentration as observed on the machine's display and approximately 0.1 to 0.2% estimated actual concentration). The material accompanying this peak is designated herein as Material Alpha. It has no known immunological activity. But its elution serves as an indication ("marker") that material designated herein as Material Beta, which has been discovered to contain an amplifier (Amplifier Beta), is about to elute.

Material Beta elutes approximately 3 minutes later, between approximately 15 and 20 minutes retention time. It is accompanied by a sharp, single ultraviolet absorption peak reaching full scale. Displayed solvent concentration is 1.2 to 2.2%; estimated solvent concentration is 0.4 to 1.5%. Immediately thereafter, at retention time between approximately 17 and 22 minutes, material designated herein as Material Gamma elutes. The Gamma Material is characterized by either a distinct broad peak of ultraviolet absorption or as a shoulder on the absorption indication at the end of the elution of Material Beta. (FIG. 1 shows Material Gamma as a distinct peak about 40% of full scale. In the runs of FIGS. ures 1A–1C, where a different Example 1 preparation was used, Gamma is only a shoulder on the descending end of Beta.) Like Material Alpha, Material Gamma is without known immunological activity.

A group of peaks are then observed in the retention time range of from 23 to 36 minutes. The first of these peaks (a rather low one, less than 30 or 40% of full scale) corresponds to (i.e., occurs with the elution of) material designated herein as Material Delta, which has been discovered to be amplifier material. Delta Material elutes in the retention time range of approximately 26–28 minutes. Displayed solvent concentration is from 3.5 to 4.0%, while estimated solvent concentration is 2.8 to 3.3%. Delta does not maintain a well-fixed location in this process, and may either not come off the column at all or be buried in the next material (Epsilon). (In the runs of FIGS. 1A–1C, Delta did not elute as a recognizable peak.)

The next large absorption peak in the group is approximately 20% (or much more) of full scale, occurs about a minute later at retention time 27–30 minutes, and is a broad single peak or a doublet; the peak accompanies material designated herein as Material Epsilon. It is without known immunological activity.

The absorption peak immediately following, approximately 2 minutes later, at retention time about 29–32 minutes, is material designated herein as Material Zeta, which has been discovered to have amplifier activity. As indicated below, Material Zeta can by a further process be separated into two moieties, Zeta-1 and Zeta-2, the second of which is has been discovered to contain the entire amplifier activity of Material Zeta (and is designated herein as Amplifier Zeta-2).

Material Eta immediately follows, about a minute later (retention time 30 to 33 minutes), accompanying the next peak. Material Eta has been discovered to contain an amplifier. Material Eta accompanies a very small broad absorption peak or a shoulder on the next and last absorption peak (Theta), which is much higher. (In FIG. 1, Material Eta is shown as a shoulder on Theta.)

Finally, Material Theta, without known immunological activity, elutes at approximately 32 to 36 minutes. It accompanies a single large absorption peak. (In some runs, Eta does not come off the column separately from Theta, but instead comes off with it. This is illustrated in FIGS. 1A–1C.)

The foregoing information is summarized in Table A, below:

TABLE A

| | HPLC Run, pH 5 Process | | | |
|---|---|---|---|---|
| Range of Retention Times (mins.) | Concentration % Display | Estim. | Ultraviolet Data | Designation |
| 12–14 | 0.5–0.9 | 0.1–0.2 | Doublet peak | Alpha |
| 15–20 | 1.2–2.2 | 0.4–1.5 | Single peak | Beta |
| 17–22 | 1.5–2.6 | 0.8–1.9 | Broad moderate peak or shoulder on end of preceding peak | Gamma |
| 26–28 | 3.5–4.0 | 2.8–3.3 | First peak of 23–36 minute group of peaks, low to moderate peak following no-absorption trough. May fail to appear. | Delta |
| 27–30 | 3.7–4.4 | 3.0–3.7 | Next large peak of 20% or more of full scale | Epsilon |
| 29–32 | 4.2–4.8 | 3.5–4.1 | Broad single | Zeta |

TABLE A-continued

| | HPLC Run, pH 5 Process | | | |
|---|---|---|---|---|
| Range of Retention Times (mins.) | Concentration % | | Ultraviolet Data | Designation |
| | Display | Estim. | | |
| 30–33 | 4.4–5.1 | 3.7–4.4 | peak or overlapping doublet Small broad peak or part of or shoulder on beginning of next peak (Theta) | Eta |
| 32–36 | 4.8–5.7 | 4.1–5.0 | Single large peak. May include Eta. | Theta |

The materials of Example 4 are contaminated with phosphate ions and are imperfectly purified from extraneous material (material having no known useful immunological activity). A further HPLC procedure with a different solvent system has been discovered to remove phosphate and extraneous material. The resulting material appears to be almost entirely free of extraneous material, and is therefore referred to by the term "Amplifier—" rather than "Material—," to distinguish such more highly purified material from less highly purified material.

EXAMPLE 5

HPLC Cleanup and Phosphate Removal

The material of preceding Example 4 was further purified and separated by HPLC on the analytic column. First, a 0.1% (v/v) aqueous trifluoroacetic acid (Mallinckrodt, Inc., Paris, Ky.) solution was prepared, and the pH of the solution was adjusted to pH 2.5 by the dropwise addition of sufficient 5M KOH aqueous solution. The solution was delivered to the Perkin Elmer machine, along with HPLC grade acetonitrile.

The machine was programmed for a 45 minute linear gradient of 0.1% to 45% concentration of acetonitrile in the trifluoroacetic acid solution. (A 25-minute run to 25% is acceptable, but 45 minutes to 45% is more conservative.) The flow rate was set at 1 ml/min.

a. Beta Run

Material Beta fractions from approximately 4 procedures of Example 4 are pooled and loaded into a "mu Bondapak" O.S. column; and HPLC is commenced. The effluents are scanned with the ultraviolet absorption detector, as in the preceding example. Full scale is set at 1.28 absorption units.

Contaminating Gamma Material elutes at 8–11 minutes and is discarded. The Gamma Material absorption peak is approximately 30–40% of full scale. Material hereinafter designated as Amplifier Beta elutes at 15–18 minutes. Its absorption peak is at least full scale and is quite sharp.

b. Zeta Run

The same procedure is repeated with Material Zeta of Example 4. Material Zeta fractionates into two moieties—hereinafter designated Zeta-1 and Zeta-2. The first is without immunological activity. The second is an amplifier. Zeta-1 elutes at approximately 11–14 minutes, Amplifier Zeta-2 at approximately 15–19 minutes. Their absorption peaks are quite sharp and are separated by an average of 2–3 minutes.

c. Eta Run

The same procedure is repeated with Material Eta of Example 4. Material hereinafter designated as Amplifier Eta elutes at approximately 18–20 minutes, accompanying a broad absorption peak (about 2 minutes wide). Contaminating Material Theta, previously mixed with the Material Eta, elutes considerably later (about 23–26 minutes as a sharp peak about 1 minute wide) and is discarded.

Figure 2A:
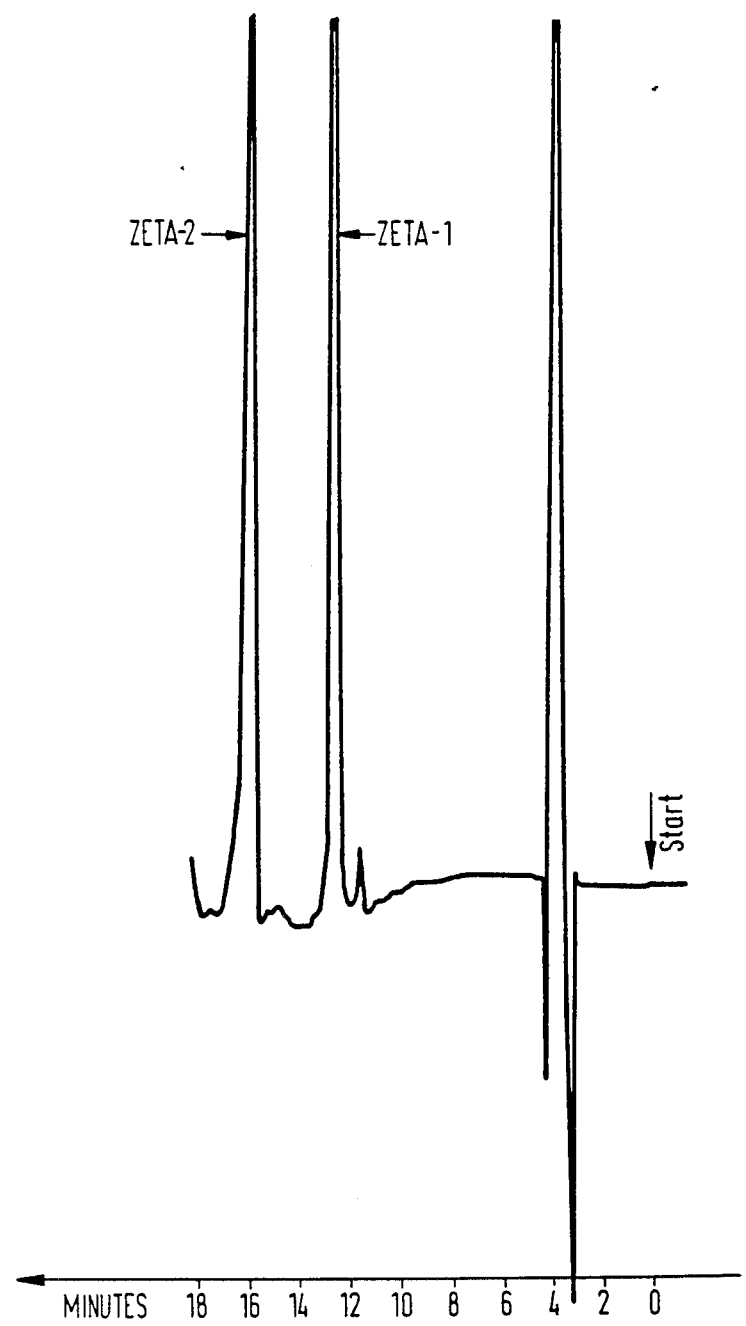
FIGS. 2A and 2B are similar graphs for runs on Material Zeta and Material Eta, respectively.
Figure 2B:
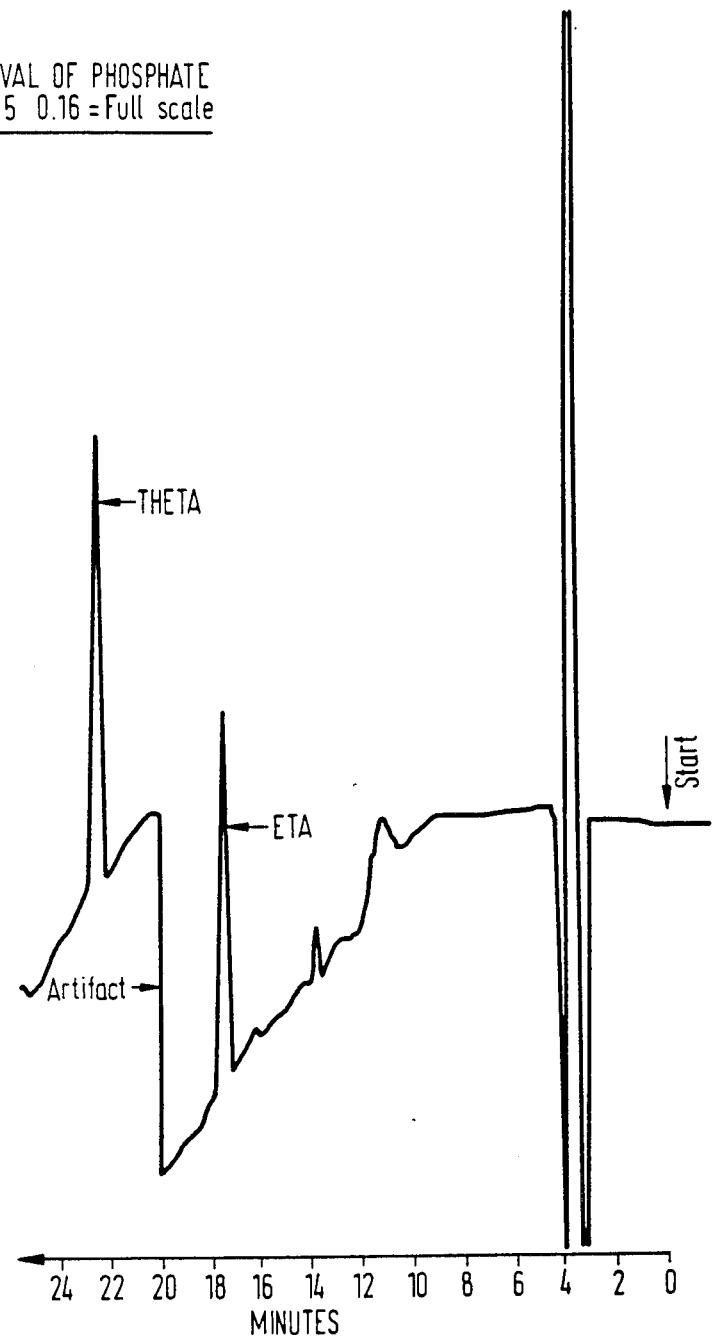

Unfortunately, Material Delta has not been recovered by use of this procedure; it may be destroyed by the trifluroacetic acid. The foregoing results are summarized in Table B, below. FIGS. 2, 2A, and 2B show the ultraviolet absorption profile of this procedure.

TABLE B

| | HPLC Cleanup | | |
|---|---|---|---|
| Range of Retention Times (mins.) | Concentration % | | Designation |
| | Display | Estim. | |
| 8–11 | 8–11 | 4.8–7.8 | Gamma |
| 11–14 | 11–14 | 7.8–10.8 | Zeta-1 |
| 15–18 | 15–18 | 11.8–14.8 | Beta |
| 15–19 | 15–19 | 11.8–15.8 | Zeta-2 |
| 18–20 | 18–20 | 14.8–16.8 | Eta |
| 23–26 | 23–26 | 19.8–22.8 | Theta |

A description of the second acetonitrile purification process (the pH 2.5 process) follows.

EXAMPLE 6

HPLC on Analytic Column, pH 2.5 Process

Material prepared in accordance with preceding Example 3 was further purified and separated by HPCL on the analytic column as follow: First, an aqueous potassium phosphate solution was prepared as in preceding Example 4, except that the pH was adjusted only to 2.5. The solution was delivered to the Perkin-Elmer machine, along with HPLC grade acetonitrile.

The machine was programmed to deliver the following three gradients: (1) 10 minutes of 0.1% to 5% concentration of acetonitrile in phosphate solution, gradient curve 4 (Perkin-Elmer LC75 program); (2) 30 minutes of 5% to 20%, gradient curve 0.2 (Perkin-Elmer LC75 program); (3) 10 minutes of 20%, constant gradient. The flow rate was set at 1 ml/min.

Then, 5–10 mg of fluram-reactive "S" fractions associated with the major fluram-reactive peak of Example 3 was loaded into a "mu Bondapak" O.S. column and HPLC was commenced.

Monitoring of ultraviolet absorption detector (full scale=0.08 units) shows nine or more peaks. The results of the run are explained below and are then summarized in Table C. Ultraviolet absorption detection at 210 nm is plotted in FIG. 3. Materials extracted by the procedure (hereinafter designated by the names Materials Pi, Sigma, and Upsilon) have been tested by the methods of the cited copending application and have been found to display amplifier activity. These effluent fractions are collected and set aside. The other fractions (hereinafter designated Materials Mu, Nu, Xi, Omicron, Rho, and Tau) are discarded.

As indicated above, during the elution process the ultraviolet absorption at 210 nm is scanned. All of the materials up to and including that associated with the fourth peak (designated herein as Materials Mu, Nu, Xi, and Omicron), eluted over an approximately 18 minute period, are discarded because they are without known amplifier activity. Xi's absorption peak is broad and goes off scale. Omicron has a sharp, approximately full scale peak. There is a deep, wide, no-absorption trough between Xi and Omicron. A small spurious peak reading may occur after Omicron as an artifact of the system; it may be disregarded.

The material of the fifth actual ultraviolet absorption peak (a doublet designated herein as Material Pi) has been found to have amplifier activity. It eluted at approximately 19.6 to 22.4 minutes and is associated with a machine display of 13.5 to 14.5% apparent solvent concentration, which corresponds to an estimated actual solvent concentration of 12.0 to 13.5%.

The sixth peak is associated with material without known activity (Material Rho). Rho is nearly full scale and it elutes as the first part of a doublet, at approximately 22.6 to 23.4 minutes.

The material of the seventh peak (Material Sigma) eluted at approximately 23.6 to 25.0 minutes and 15.3 to 15.8% apparent concentration. Sigma is the second, usually lesser, part of a doublet with Rho, which immediately precedes it. Material Sigma possesses amplifier activity.

The eighth peak is associated with material without known activity (Material Tau). It is an indistinct peak on the trailing edge of Sigma.

The material of the ninth peak (Material Upsilon) eluted at approximately 28.2 to 29.2 minutes and 16.8 to 17.1% apparent concentration. It possesses amplifier activity. Upsilon is the next major, distinct peak after Tau. It is followed by several indistinct lower peaks not associated with material of interest.

The data relating to the elution of these amplifier materials is summarized below in Table C.

TABLE C

| Retention Times (Mins.) | HPLC Run, pH 2.5 Process | | | Designation |
|---|---|---|---|---|
| | Concentration % | | Ultraviolet Data | |
| | Display | Estim. | | |
| 0–18 | 0.1–12.6 | 0.1–11.3 | 4 peaks | Mu, Nu, Xi Omicron |
| 19.6–22.4 | 13.5–14.5 | 12.0–13.5 | 2 small peaks | Pi |
| 22.6–23.4 | 14.8–15.0 | 13.8–13.9 | First large peak of a doublet with Sigma | Rho |
| 23.6–25.0 | 15.3–15.8 | 14.0–14.5 | Large second peak of Rho doublet | Sigma |
| 25–28 | 15.8–16.7 | 14.5–15.6 | Indistinct trailing peak on end of Sigma | Tau |
| 28.2–29.2 | 16.8–17.1 | 15.8–16.0 | Next large peak after Tau | Upsilon |

Biological Assay Data

Additional biological assay methods have been developed, which were not described in the cited copending application. The cited copending application describes assaying amplifier material by the enhanced DH response in normal subjects when re-exposed to an antigen. In addition, the following assay methods have now been found advantageous:

(1) antigen-induced enhanced "leukocyte inhibitory factor" ("LIF");

(2) augmented production of interleukin-2, ("IL-2")stimulated by mitogen or alloantigen; and (3) enhanced generation of cytotoxic cells to Raji cells.

It has been found that Materials Beta and Zeta-2 display at least two out of three of the new assay criteria as well as the enhanced DH response of the cited copending application. Beta displays all three; Zeta-2 has not yet been tested with the LIF assay. Delta has been found to enhance mitogen-induced IL-2 production. Eta enhances generation of cytotoxic cells to Raji cells. Materials Delta, Eta, Pi, Sigma, and Upsilon have been found to display the enhanced DH response of the cited copending application, but have not been otherwise tested as yet with the three newer assay procedures.

The protocol for the enhanced DH assay is given in the cited copending application. The LIF assay is described in Gottlieb et al., *Modulation of Human T Cell Production*, J. Immunology 132:256–260 (January 1984), at p. 257. A procedure for the mitogen IL-2 assay is described in a paper of Gottlieb et al., *Reconstitution of T Cell Function in AIDS Patients by Use of a Leukocyte-Derived Endogeneous Immunolmodulator*, which the inventor anticipates will shortly be published. A copy of this paper is transmitted with the application for inclusion in the file wrapper. Protocols for the alloantigen IL-2 assay and Raji cell assay are believed to be known to those skilled in this art, but copies of such protocols are nonetheless transmitted with the application for inclusion in the file wrapper.

As indicated above, it has been shown that the amplifier materials of this invention have amplifier activity. This was done by means of the DH assay of the cited copending application. Examples 7–9 illustrate three such assays.

EXAMPLE 7

DH Assay of Beta

Serial dilutions of Amplifier Beta preparations of preceding Example 5 were made from a solution containing the amplifier material derived from 400,000,000 buffy coat leukocytes in 1 ml of aqueous saline solution.

Tetanus toxoid was selected as the antigen to challenge the immune system of the patient. To 0.05 ml of tetanus toxoid, fluid diluted to $\frac{1}{2}$ to 1/10 so as to elicit a small (preferably slightly less than 5×5 mm) skin reaction from the patient, 0.1 ml of the diluted Amplifier Beta preparation was added. The patient was subcutaneously injected with several different dilutions of Amplifier Beta, and also with an equal quantity of tetanus toxoid (TT) without any Amplifier Beta added thereto. Two approximately perpendicular diameters of each responding skin site on the man's arm were measured at the times indicated below. ("TT+—" refers to TT and a dilution of Beta to the concentration indicated; "TT" alone is TT without Beta.)

At 5 hours, the respective responses to $TT+10^{-8}$, $TT+10^{-9}$, and TT were 14×14 mm, 19×14, and 3×3. At 24 hours: 20×24 mm, 19×23, 14×12.

EXAMPLE 8

DH Assay of Delta

The procedure of Example 7 is repeated with Material Delta of Example 4.

At 6 hours, the respective responses to $TT+10^{-7}$ and TT were 19×18 mm, 13×11. At 23 hours: 28×29 mm, 7×6.

EXAMPLE 9

DH Assay of Zeta

The procedure of Example 7 is repeated with Amplifier Zeta-2 of Example 5. However, purified protein derivative of tuberculin ("PPD") was substituted for TT.

At 12 hours, the respective responses to $PPD+10^{-6}$, $PPD+10^{-7}$, $PPD+10^{-8}$, and PPD were $1\times1$ mm, $15\times22$, $14\times11$, and $1\times1$. At 27 hours: $2\times2$ mm, $22\times24$, $15\times15$, and $3\times3$.

EXAMPLE 10

DH Assay of Eta

The procedure of Example 7 is repeated with Amplifier Eta of Example 5.

At 4 hours, the respective responses to $TT+10^{-3}$, $TT+10^{-4}$, $TT+10^{-5}$, $TT+10^{-6}$, and TT were $2\times3$ mm, $7\times7$, $2\times3$, $3\times3$, and $2\times2$. At 13 hours: $8\times11$ mm, $16\times20$, $16\times15$, $4\times5$, and $6\times4$.

EXAMPLE 11

DH Assay of Pi

The procedure of Example 7 is repeated with Material Pi of Example 6.

At 6 hours, the respective responses to $TT+10^{-7}$, $TT+10^{-8}$, $TT+10^{-9}$, and TT were $8\times10$ mm, $12\times11$, $7\times8$, and $2\times3$. At 21 hours: $12\times12$ mm, $21\times15$, $15\times16$, and $14\times13$.

EXAMPLE 12

DH Assay of Sigma

The procedure of Example 7 is repeated with Material Sigma of Example 6.

At 4 hours, the respective responses to $TT+10^{-7}$, $TT+10^{-8}$, $TT+10^{-9}$, and TT were $12\times11$ mm, $13\times12$, $4\times2$, and $4\times2$. At 8.5 hours: $17\times15$ mm, $19\times20$, $5\times4$, and $5\times4$.

EXAMPLE 13

DH Assay of Upsilon

The procedure of Example 7 is repeated with Material Upsilon of Example 6.

At 5.5 hours, the respective responses to $TT+10^{-1}$ and TT were $16\times13$ mm, $10\times8$. At 9 hours: $15\times25$, $13\times10$. At 11 hours: $25\times23$, $12\times15$.

Human Tests

The effectiveness of the amplifier material of this invention in amplifying human immune system response has been tested in a number of men suffering from acquired immune deficiency syndrome (AIDS) or the AIDS-Related Complex (ARC). All amplifier materials used in this work were free of endotoxin as detected by the Limulus assay (M.A. Bioproducts, Rockville, Md.).

EXAMPLE 14

Single Dose

Three AIDS patients with Kaposi's sarcoma, TM, JF, and RC, were each given a single subcutaneous dose of Amplifier Beta. The dose contained the amount derived from 400,000 leukocytes, purified by the method of Example 5 and dispensed in 0.5 ml of normal sterile saline solution.

All three patients exhibited enhanced phytohemagglutin (PHA) proliferative responses following the dose. In the case of one patient, JF, sufficient peripheral blood lymphocytes (PBLs) were made available to permit further study. Increased production of IL-2 in response to PHA was observed in JF, and also modulation of IL-2 production by Amplifier Beta, in vitro. No significant changes were observed in skin test response to tetanus toxoid or in lymphocyte subpopulation by fluorescence activated cell sorter (FACS) analysis.

EXAMPLE 15

Multiple Doses

A fourth AIDS patient with Kaposi's sarcoma, DT, was given doses of Amplifier Beta together with transfusions of isologous leukocytes available from DT's identical twin brother (a normal, disease-free person). DT also received such transfusions without Amplifier Beta.

An initial transfusion of $10^{10}$ isologous leukocytes (without Amplifier Beta) produced a moderate restoration of DT's phytohemagglutin (PHA) proliferative response. Within 13 days the response declined to baseline levels with no concomitant alteration in the ratio of circulating helper lymphocytes to suppressor lymphocytes (T4/T8 ratio).

Ten days after the initial transfusion, DT was given a single dose of Amplifier Beta (derived from 400,000 leukocytes). No effect was observed on DT's PHA response.

A cycle of treatment comprised of a second isologous leukocyte transfusion (again, $10^{10}$ leukocytes) followed at 24, 48, and 71 hours by subcutaneous Amplifier Beta doses derived from 400,000, 4,000,000, and 400,000 leukocytes, respectively. A significant increase in DT's PHA responsiveness followed. It was associated with an increase in the T4/T8 ratio, resulting from an absolute increase of T4+ cells and a decrease in T8+ cell numbers. After approximately one month, these parameters of immune system response declined to approximately their former level.

A third transfusion similar to the first (no Amplifier Beta) was given. No effect on PHA response or T4/T8 ratio was observed.

While these studies were made, parallel studies of IL-2 production were made. Initially, no IL-2 production was observed in response to PHA. This correlated with the patient's low proliferative response to mitogen. The initial leukocyte transfusion did not affect this parameter. After the second transfusion (leukocytes and Amplifier Beta), significant levels of IL-2 were induced by PHA. A more detailed presentation of the experimental data concerning DT is found in the Gottlieb et al. paper, *Reconstitution of T-cell Function in AIDS Patients*, transmitted with the application.

From these and other tests, the inventor believes that Amplifier Beta acts on the T4+ helper cell population of the human body. This suggests that Amplifier Beta is useful in improving human immune response characterized by a T4+ defect. It is believed that doses of Amplifier Beta partially restore the functioning of a defective subset of the T4+ lymphocytes. Tests such as those on patient DT suggest that Amplifier Beta can partially correct a defect in T4+ cell function even in the presence of the excessive proportions of T8+ cells observed in AIDS patients. It appears, further, that some minimal level of residual T4+ cell function must be present for Amplifier Beta to improve immunological functions; if T4+ loss is too severe, there may not be enough T4+ cells left to respond to doses of Amplifier Beta and thus be immunologically reconstituted.

EXAMPLE 16

Increase of Immune Response

Amplifiers are prepared and purified as described in Example 5, and are pooled, lyophilized, and redissolved in normal saline or other physiologically acceptable vehicle. An effective dose, e.g., 0.1 ml containing the equivalent amount of amplifiers purified from $5 \times 10^7$ leukocytes, is injected subcutaneously. Increased immune responsiveness is monitored by the patient's reactivity to an antigen to which he is known to be sensitive (e.g., tetanus toxoid), comparing reactivity before and after administering the amplifiers.

Amplifiers are administered either individually, or in combination, depending upon the desired effects. The persistence of the systemic modulation produced by administration of the amplifiers varies from patient to patient, and must therefore be monitored periodically with a suitable sensitivity test, e.g., as described above. Additional doses are administered as required to maintain a desired amplification of immunity based upon the professional judgment of the attending physician.

Use of Dermal Patch

It has been found advantageous to cause dermal absorption of amplifier material, rather than inject it subcutaneously. Such administration is faster, requires less skill, and is somewhat less annoying to patients. Also, a dose of amplifier material may be administered more slowly by this route, so that there is a more long lasting therapeutic effect.

EXAMPLE 17

Patch Application of Amplifiers

A patient suffering from immune system deficiency is treated with Amplifier Beta of preceding Example 5, as follows. The patient's forearm is cleansed with 70% isopropyl alcohol and permitted to dry. An emery board (drugstore type), which has previously been presterilized by autoclaving, is used gently to abrade the patient's skin surface; the skin is stroked 5–6 times with the board. The skin area is recleansed with 70% isopropyl alcohol and permitted to dry.

A medically determined dosage of Amplifier Beta of Example 5 is diluted to an appropriate dose, in accordance with Example 12, and is placed on the gauze portion of a small sterile bandage strip (e.g., Johnson & Johnson "Band-Aid"), approximately 25 mm × 15 mm, which is then applied over the abraded area.

While a medically determined dosage is a matter of the discretion of the prescribing physician, a dose of Amplifier Beta derived from approximately 400,000 leukocytes is believed appropriate.

The same procedure is used with Amplifier Eta, Amplifier Theta-2, and other amplifier materials.

Vaccines

The amplifiers, either singly or in combination, can be used to produce an immune response to weak vaccines. Many pathogens, including several Staphylococcus varieties and fungi responsible for Histoplasmosis or Candidiasis, fail to provoke a strong immune response in certain patients. Moreover, there is no known satisfactory vaccine for conferring immunity on such patients. Such fungal infections are especially dangerous for patients subjected to cancer chemotherapy, or immunosuppressive drugs.

By enhancing the patients' immune response to weak antigens, however, the concurrent administration of the described amplifiers, either singly or in combination, makes it possible to prepare vaccines against such pathogens. Patients about to receive chemotherapy or transplant surgery can thus be vaccinated prior to treatment, to reduce their susceptibility to histoplasmosis or candidiasis. Used as described below, amplifiers are expected to expand the scope of preventative measures in medicine, and to enlarge the range of weak antigens which can be used for immunization.

EXAMPLE 18

Vaccination

Vaccine is preferably prepared by combining amplifier materials of Examples 4, 5, or 6 with antigens of the desired pathogen, prepared according to known methods in the art to ensure adequate attenuation and sterility. The vaccine is then administered by standard procedures.

Discussion of Preceding Data

On the basis of the foregoing data, it is possible to characterize Amplifier Beta and the other amplifier materials of this invention more precisely. It is also possible to describe more precisely the procedures for purifying them and separating them from one another and from other materials.

These amplifier materials are all characterized by (a) M.W. under 3500, and (b) being O.S. elutable with an acetonitrile-in-phosphate gradient of appropriate pH. (As used hereinafter, "O.S. elutable" with an acetonitrile-in-phosphate gradient means: capable of being eluted from octadecyl silane by means of reverse-phase high pressure liquid chromatography with an acetonitrile-in-phosphate gradient of increasing acetonitrile concentration.) The property or parameter of being O.S. elutable permits the further characterization and separation of these amplifier materials because they can be ordered in terms of their relative elutability. Amplifier Beta, for example, is O.S. elutable in the portion of the gradient containing only 0.4–1.5% acetonitrile in the effluent. Amplifier Zeta-2 is O.S. elutable only in a much greater concentration of acetonitrile, and so on. Moreover, it appears that a higher acetonitrile concentration is required in a more acid solution, which suggests some guideline for future trial and error development of additional HPLC gradient systems.

Each of these amplifier materials can therefore be characterized in terms of several parameters:

(1) the given amplifier material is primarily O.S. elutable in a specific zone of the gradient, from lower acetonitrile concentration limit a to upper concentration limit b;

(2) The amplifier material is primarily not O.S. elutable in the zone of the gradient below a;

(3) the amplifier, when properly purified from extraneous material, is substantially free of material that is O.S. elutable in the zone below a;

(4) the amplifier, when properly purified from extraneous material, is substantially free of material that is O.S. elutable primarily in the zone above b; and (5) for any given amplifier material there may be an inverse correlation between gradient pH and acetonitrile concentration defining the elution zone of the gradient.

The third and fourth items may warrant further explanation. If an acetonitrile-in-phosphate gradient is used that begins at a concentration in the middle or upper part of the range, e.g., 10%, then the first fraction that comes off will contain substantially all of the material O.S. elutable from 0 to 10%. Therefore, to properly purify material O.S. elutable from 10% to 12%, the gradient should begin below 10%, e.g., at 7% or 0%, so that all the material elutable in acetonitrile less concentrated than 10% will come off the column before the material elutable at 10% to 12% begins to come off. Otherwise, an ineffective purification will occur. This explains the presence of item (3) above.

The fourth item states a characteristic that should automatically occur in any procedure using a gradient of increasing concentration. If the gradient begins, e.g., at 10% or below, and stops at 12% or above, what elutes between 10% and 12% will be largely free of material O.S. elutable primarily at higher acetonitrile concentrations, such as 15%. This indicates, of course, that acetonitrile concentration in the gradient should always monotonically increase with time, in a proper purification procedure. That is the customary methodology.

Furthermore, any given amplifier can be characterized in terms of the ultraviolet absorption profile. Measurement at 210 nm is preferred because that wave length represents a peptide bond that is apparently characteristic of these substances. The profile has been found to be a good indicator, although there is some difficulty in articulating the criterion with precision. FIGS. 1 to 3 will assist those of skill in the field to recognize where particular materials will elute, despite variations in HPLC parameters, in that the figures provide at the very least an "I know it when I see it" criterion. In the discussion that follows, a more precise characterization of the amplifier materials of this invention in terms of the ultraviolet absorption profile is set forth. The foregoing descriptive and characterization data for the S-fraction amplifiers materials can be summarized and explained as follows:

Amplifier Beta

Amplifier Beta is characterized as having both an accelerating and augmenting effect on the DH skin response of recipients sensitive to a given antigen. See Example 7. The reactions produced by Amplifier Beta administered with antigen reach peak intensity at about 6 to 24 hours after subcutaneous injection and fade rapidly thereafter. (In contrast, normal DH response, in the absence of amplifier, reaches a peak 24 to 30 hours after injection of antigen.) Maximal amplifying activity is observable at an optimum concentration, with greater or lesser concentrations giving a reduced amplification of DH response.

Amplifier Beta is O.S. elutable as Material Beta between approximately 0.4% to 1.5% (v/v) acetonitrile concentration, that is, in the portion of the pH 5 acetonitrile-in-phosphate HPLC gradient where the effluent has a refractive index of from approximately 1.330 to 1.333. Material Beta is characterizable in terms of its ultraviolet absorption profile in the pH 5 process as a distinct peak following a doublet peak (Alpha) and preceding a distinct broad lower peak (Gamma) or a shoulder (also Gamma) on its own peak. Gamma is followed by an interval (trough) without substantial ultraviolet absorption.

Amplifier Beta passes through a dialysis membrane having a nominal M.W. cutoff of 3500, so that the M.W. of Amplifier Beta may be presumed to be less than 3500. Amplifier Beta may be the same as, or a moiety of, Amplifier 1 of the cited copending application.

Material Delta

Material Delta causes augmented and prolonged response to antigen. See Example 8. Delta's biological activity is generally similar to Beta's.

Material Delta elutes from the pH 5 gradient where the acetonitrile concentration is approximately 2.8 to 3.3%. Material Delta is characterizable in terms of its ultraviolet absorption profile in the pH 5 process as the first distinct peak in a group of three peaks following the space (trough) in the absorption profile after the Gamma peak or shoulder. However, Delta is not always recovered separately in the pH 5 process, particularly if the pH is off.

It is not recoverable from the 2.5 pH trifluoracetic acid cleanup process of Example 5. It may have bonds susceptible to acid hydrolysis.

Amplifier Zeta-2

Amplifier Zeta-2 also causes both an accelerated and augmented response to antigen, and is generally similar to Beta in activity, although the degree of acceleration is somewhat less rapid than the response to Amplifier Beta. Maximal amplifying activity with Amplifier Zeta-2, as with Beta, is observable only at an optimum concentration, with greater than optimal concentrations giving reduced amplification or even suppression of the DH response.

Amplifier Zeta-2 is O.S. elutable as Material Zeta in the portions of the pH 5 acetonitrile-in-phosphate gradient between approximately 3.5 to 4.1%, where the refractive index of the effluent is from approximately 1.344 to 1.345. Material Zeta is characterizable in terms of its ultraviolet absorption profile in the pH 5 process as the last of a distinct group of three peaks (two, if Delta fails to come off) following the space (trough) in the absorption profile after the Gamma peak or shoulder, and preceding either a shoulder (Eta) on a distinct broad peak (Theta) or else preceding a small peak (Eta) followed by a distinct broad peak (Theta). In the cleanup process of Example 5, Zeta-2 is the third major peak.

Amplifier Eta

Amplifier Eta also causes both an accelerated and augmented response to antigen, and is generally similar to Beta, although the degree of acceleration appears to be somewhat less rapid than the response to Amplifier Beta.

Amplifier Eta is O.S. elutable as Material Eta in the portions of the pH 5 acetonitrile-in-phosphate gradient between approximately 3.7 to 4.4%, where the refractive index of the effluent is from approximately 1.347 to 1.353. Material Eta is characterizable in terms of its ultraviolet absorption profile in the pH 5 process as following the last (Zeta) of a distinct group of three (two, if Delta fails to come off) peaks following the space (trough) in the absorption profile after the Gamma peak or shoulder, and as being a small broad peak or a shoulder preceding (or included in) a distinct broad peak (Theta).

Material Pi

Material Pi also causes both an accelerated and augmented response to antigen, generally similar to Material Beta. Material Pi is O.S. elutable in the portions of the pH 2.5 acetonitrile-in-phosphate gradient between approximately 12.0 to 13.5%. Material Pi is characterizable in terms of its ultraviolet absorption profile in the pH 2.5 process as a doublet peak in the fifth position among nine peaks. Typically, Pi is preceded by a higher peak (Omicron) and followed by two close, higher peaks (Rho and Sigma). The Omicron peak is preceded by a deep trough.

Material Sigma

Material Sigma also causes both an accelerated and augmented response to antigen, generally similar to Material Beta, although the degree of acceleration appears to be somewhat less rapid than the response to Amplifier Beta. Material Sigma is O.S. elutable in the portions of the pH 2.5 acetonitrile-in-phosphate gradient between approximately 14.0 to 14.5%. Material Sigma is characterizable in terms of its ultraviolet absorption profile in the pH 2.5 process as the seventh of nine peaks, typically preceded very closely by a higher peak (Rho) and followed by a lower peak or trailing shoulder (Tau) and then a distinct high peak (Upsilon). It is possible that Material Sigma of the pH 2.5 process may be the same material as Material Beta of the pH 5 process.

Material Upsilon

Material Upsilon causes an augmented DH response and is generally similar to Material Beta in activity. See Example 9. Material Upsilon elutes at approximately 15.8 to 16.0 acetonitrile concentration in the pH 2.5 process.

Material Upsilon is characterizable in terms of its ultraviolet absorption profile in the pH 2.5 process as the ninth of nine peaks, following a descending profile trailing the seventh peak (Sigma); the descending profile is interrupted by a lesser peak or a shoulder (Tau). It is possible that Material Upsilon of the pH 2.5 process may be the same material as Material Delta of the pH 5 process.

Comparison of Present Amplifiers with Those of Cited Copending Application

Amplifier Beta has been purified as described above and then subjected to the ethanol-water HPLC process of the cited copending application. The results show elution of Beta in the same region of the gradient as Amplifier 1 of the cited copending application. This suggests, but does not establish, that Amplifier Beta is Amplifier 1 or a moiety thereof. It is also possible that Amplifier Beta simply happens to have the same ethanol-water HPLC elution characteristics as Amplifier 1 of the cited copending application. Amplifiers Beta and 1 have similar biological activity, but they do not appear to have identical activity.

GENERAL CONCLUDING REMARKS

The above described amplifiers of the immune system are considered to be materials whose natural function is regulation of the immune response, directly with respect to cell mediated immunity and perhaps indirectly affecting humoral immunity as well. The materials have been prepared with a high degree of purity such that their properties have now been characterized and shown to be entirely and unexpectedly different from transfer factor and from partial fractionations thereof reported in the prior art. It will be understood, however, that the materials disclosed and claimed herein are defined in terms of their biological activities and physical properties and do not necessarily consist of single molecules or chemical entities.

The amplifier materials herein described are medically useful for the treatment of patients suffering from a variety of hypoimmune conditions. It is especially significant that these materials may be isolated from normal individuals, rather than from specific identified donors, so that large-scale purification from pooled sources is feasible.

The invention is also considered to include the novel processes for purification and extraction of these new materials, described herein, as well as the novel compositions including these materials and the methods using them, disclosed herein. The development of several HPLC acetonitrile processes has provided some general principles for determining the identity of other similar systems, and it is considered that the scope of the invention includes other HPLC systems in conformity with such principles.

First, it is not critical what the exact shape of the gradient is. Rather, it is important to determine where in the gradient the materials of interest come off the column. That part of the gradient should not be crowded, so that $dc/dt$, where c represents solvent concentration, should have a relatively low value at the points where materials of interest come off (and preceding such points, because of the lag effect previously mentioned). Therefore, the gradient curve should be relatively flat at and before points where useful material comes off or a separation of materials is desired. If a single gradient curve meets this requirement, it may be selected. Otherwise, a series of curves should be joined (as in Examples 4 and 6).

Second, the pH must be adjusted to provide a good yield for the solvent system used. As previously indicated, there appears to be an inverse correlation of pH and acetonitrile concentration for effective separation in this process. The proper pH adjustment is a matter of trial and error.

Third, phosphate buffer has been found effective for this procedure, at 0.02 M. If a different concentration of buffer is used, or a different acidic ion such as acetate or sulfate, then the solvent concentrations and the proper adjustment of pH will be different. Compare Examples 4, 5, and 6.

Fourth, a relatively basic buffer (see Example 4) leaves ionic contaminants and extraneous material in the fractions of interest. The former may have to be removed (see Example 5). On the other hand, a relatively acidic buffer may destroy some materials of interest (see Example 5).

Finally, in evaluating a particular acetonitrile-in-aqueous-phosphate gradient, the ultraviolet absorption profile is very helpful in determining whether a good separation is being achieved.

While the invention has been described in connection with specific and preferred embodiments thereof, it will be understood that it is capable of further modifications without departing from the spirit and scope of the invention. This application is intended to cover all variations, uses, or adaptations of the invention, following, in general, the principles of the invention and including such departures from the present disclosure as come within known or customary practice within the art to which the invention pertains.

Brief Discussion of Claims Presented for Examination Terminology

The claims presented hereinafter are intended to describe the subject matter hereinbefore disclosed. The lexicography, insofar as it differs at all from ordinary usage is based on the preceding disclosure and should be understood in the light thereof.

The terms "dialysis" and "gel filtration" are intended to include their equivalents. Thus, "dialysis" as used herein includes ultrafiltration, ultracentrifugation, and electrophoresis. ("Dialysate" means the low M.W. product of any such procedure.) "Gel filtration" includes gel exclusion chromatography on a higher performance liquid chromatographic system.

The term "pH-adjusted" refers to alteration of pH with base, acid, or buffer, such as in Examples 4, 5, and 6. The term "aqueous-phosphate-solution" refers to an alkali or alkaline earth (strong base such as K, Na, Ca, etc.) phosphate buffer or solution such as that described in Examples 4 and 6. Concentration percentages for gradients are expressed on a (v/v) basis.

The term "extraneous material" refers to material not having the amplifier activity to which the invention is directed. The term "amplifier material" refers to a composition largely purified of extraneous material, but not necessarily nearly 100% so purified. The term "purified" does not necessarily mean nearly 100% purified of extraneous material, but the term "substantially purified" is intended to mean nearly entirely free of extraneous material, within the limits of the technology described hereinbefore.

A term such as "Material __," where the space is replaced by a Greek letter, refers to a largely (or possibly, but not necessarily, nearly entirely) purified material. A term such as "Amplifier __," where the space is replaced by a Greek letter, refers to a substantially purified amplifier, nearly entirely free of extraneous material, within the limits of the technology described hereinbefore. Refractive indices are given for 26° C. and ordinary incandescent light.

The term "UVPP" ("ultraviolet profile position") is used to characterize amplifier materials in terms of where they come off the HPLC column, in relation to other materials coming off the column, and using the shape of the ultraviolet absorption profile as the frame of reference. Thus, if the ultraviolet absorption profile of a process resembled the profile of a human face, one could define a particular material, for example, as that material which eluted when the ultraviolet absorption reading corresponded to the tip of the nose on the ultraviolet absorption profile. The UVPP of that particular material would be: "at the tip of the nose." The UVPP of the hypothetical material would remain recognizable, even though the profile were modified by an increase or decrease in flow rate or by a change in gradient curve. To those skilled in the art, the topological characteristics of the profile would make it recognizable despite the distortions introduced by modifying the gradient, and the tip of the nose could still be located.

Hence, the term "UVPP" as used hereinafter refers to the topological characteristics (and to some extent also the relative magnitudes of ultraviolet absorption peaks) of the ultraviolet absorption profile of the effluent passing the ultraviolet absorption detector of the machine, in the course of an HPLC procedure wherein solvent concentration monotonically increases with time. The characteristics are expressed relative to the characteristics of materials eluting nearby in the gradient in the course of the procedure. UVPP must be stated with reference to a specific gradient, such as acetonitrile-in-aqueous-phosphate-solution of a particular pH. UVPP data has been provided above in the "Discussion of Preceding Data" section of the specification, in the descriptions of the individual amplifier materials. As noted previously, material passes the ultraviolet absorption detector slightly before leaving the column (e.g., 48 seconds earlier for a 1 ml/min flow rate and a 0.8 ml volume of post-detector tubing).

Claim 1 is a generic process claim, directed to the extraction of amplifier materials by using a pH-adjusted acetonitrile-in-aqueous-phosphate-solution gradient in HPLC, as taught hereinabove. Claim 2 describes the same process with the additional limitation that the pH be 2.5, and that a 0.1% to 20% acetonitrile concentration, 0.02M phosphate buffer (strong base such as K, Na, Ca, etc.) solvent system be used. (See Example 6.)

Claim 3 is also dependent on claim 1; it adds the limitation that the pH be 5, and that a 0.1% to 15% acetonitrile concentration, 0.02 M phosphate buffer solvent system be used. (See Example 4.)

Claims 4 to 7 are each dependent on claim 3 and are respectively directed to the Materials Beta, Delta, Zeta, and Eta extractions of the process of Example 4. (See also Table A.)

Claim 8 is dependent on claim 3 and adds the further steps of the general cleanup and purification process of Example 5. Claim 9 is dependent on claim 8 and adds the further limitation that the pH be 2.5, and that a 0.1% to 25% acetonitrile concentration, 0.1% trifluoracetic acid solution solvent system be used. (See Example 5.)

Claims 10 to 12 are each dependent on claim 9, and are respectively directed to the Amplifiers Beta, Zeta-2, and Eta extractions of the process of Example 5. (See also Table B.)

Claim 13 is dependent on claim 1 and adds to that process the gel-filtration and fluram analysis steps of Examples 2 and 3. Claim 14 is dependent on claim 13 and adds the pH 5, etc. limitations stated in claim 3.

Claim 15 is also dependent on claim 13, and adds the pH 2.5, etc. limitations stated in claim 2. (This is the process of Example 6.)

Claims 16 to 18 are each dependent on claim 15, and are respectively directed to the Materials Pi, Sigma, and Upsilon extractions of the process of Example 6. (See also Table C.)

Claim 19 is an independent claim generically directed to the amplifier materials disclosed herein, characterizing them in terms of molecular weight, amplifying immunological properties, molecular structure making them elutable in acetonitrile, etc., as disclosed hereinabove.

Claim 20 is dependent on claim 19, and includes the further limitations that the material be elutable in a pH 5 phosphate buffer system with acetonitrile concentrations between approximately 0 and 15%. (See Example 4.)

Claims 21 to 24 are dependent on claim 20, and are directed to Materials Beta, Delta, Zeta, and Eta, characterizing them in terms of their specific elutability properties, as described hereinabove. (See Example 4 and Table A.)

Claim 25 is dependent on claim 19, and includes the further limitations that the material be elutable in a pH 2.5 phosphate buffer system with acetonitrile concentrations between approximately 0 and 20%. (See Example 6.)

Claims 26 to 28 are dependent on claim 25, and are directed to Materials Pi, Sigma, and Upsilon, characterizing them in terms of their specific elutability properties, as described hereinabove. (See Example 6 and Table C.)

Claim 29 is dependent on claim 20, with the further limitation that the material is also capable of being eluted with an acetonitrile-in-trifluoroacetic-acid gradient, as in Example 5. Claim 30 is dependent on claim 29, with the further limitations that the material be elutable in a pH 2.5, 0.1% trifluoroacetic acid system with acetonitrile concentrations between 0% and 25%, as in Example 5.

Claims 31 to 33 are dependent on claim 30, and are directed to Amplifiers Beta, Eta, and Theta-2, characterizing them in terms of their specific elutabiltiy properties, as described hereinabove. (See Example 5 and Table B.)

Claim 34 is directed to a pharaceutical composition containing amplifier material of claim 19. (See Example 16.) Claim 35 is dependent on claim 34, having the further limitation that the amplifier material is one of Amplifiers Beta, Zeta-2, or Eta. (See Example 16.)

Claim 36 is dependent on claim 34. It is directed to the vaccine of Example 18. Claim 37 is dependent on claim 36, and requires that the amplifier used in the vaccine be one of Amplifiers Beta, Zeta-2, or Eta.

Claim 38 covers the method of amplifying immunological function in a patient with a hypoimmune condition by treating the patient with amplifier material of claim 19. (See Example 16.) Claim 39 is dependent on claim 38, limiting the amplifier material to one of Amplifiers Beta, Zeta-2, or Eta. (See Example 16.)

Claim 40 covers the method of treating a hypoimmune condition or immune system deficiency disease by administering amplifier material of claim 19 to the patient. (See Example 16.) Claim 41 is dependent on claim 40, and limits the disease to AIDS or ARC. (See Examples 14–15.)

Claim 42 is dependent on claim 40, and limits the disease to one associated with T4+ cell function defects. (See discussion following Example 15.) Claim 43 is dependent on claim 42, and adds the limitation of a further step of also giving a T4+ transfusion to the patient. (See Example 15.) Claim 44 is dependent on claim 40 and requires dosage to be via a skin pad (as in Example 17). Claim 45 is dependent on claim 40 and limits the amplifier material to one of Amplifiers Beta, Zeta-2, or Eta. (See Example 17.)

Claim 46 is dependent on claim 20 and characterizes Material Beta in terms of its UVPP. Claims 47 to 49 are similar and are directed to materials Delta, Zeta, and Eta. The UVPP data comes from Table A and the preceding discussion, and also the "Discussion of Preceding Data" section of the specification. See also FIGS. 1, 1A, 1B, and 1C.

Claim 50 is dependent on claim 25 and characterizes Material Pi in terms of its UVPP. Claims 51 and 52 are similar and are directed to Materials Sigma and Upsilon. The UVPP data comes from Table C and the preceding discussion, and also the "Discussion of Preceding Data" section of the specification. See also FIG. 3.

The following is claimed as subject matter:

1. A process of purifying amplifier material from an extract of human leukocytes, and of separating said material from substantially all fluorescamine-reactive material and from other extraneous material, comprising the steps of:
   (1) dialyzing said extract through a dialysis membrane having a nominal molecular weight cutoff of about 3500, thereby producing a dialysate;
   (2) applying said dialysate to a reverse-phase high pressure liquid chromatography column, packed with octadecylsilane;
   (3) eluting said column with a pH-adjusted acetonitrile-in-aqueous-phosphate-solution gradient, thereby producing a plurality of effluent-fractions; and
   (4) selecting predetermined effluent-fractions, and collecting them.

2. The process of claim 1 wherein said aqueous-phosphate solution is approximately 0.02 M phosphate, the pH thereof is adjusted to approximately 2.5, and the acetonitrile concentration of said gradient includes the range from approximately above 0% to approximately 20%.

3. The process of claim 1 wherein said aqueous-phosphate solution is approximately 0.02 M phosphate, the pH thereof is adjusted to approximately 5, and the acetonitrile concentration of said gradient includes the range from approximately above 0% to approximately 15%.

4. The process of claim 3 wherein:
   (a) said gradient includes acetonitrile from below a concentration of approximately 0.2% to at least approximately 2%, and
   (b) said selected and collected effluent-fractions are those having a refractive index between approximately 1.330 and approximately 1.333
whereby an amplifier material herein designated "Material Beta" is extracted in purified form.

5. The process of claim 3 wherein:
   (a) said gradient includes acetonitrile from a concentration of approximately 2% to at least approximately 4%, and
   (b) said selected and collected effluent-fractions are those having a refractive index between approximately 1.333 and approximately 1.335
whereby an amplifier material herein designated "Material Delta" is extracted in purified form.

6. The process of claim 3 wherein:
   (a) said gradient includes acetonitrile from below approximately 3% to at least approximately 5%, and
   (b) said selected and collected effluent-fractions are those having a refractive index between approximately 1.344 and approximately 1.345
whereby an amplifier material herein designated "Material Zeta" is extracted in purified form.

7. The process of claim 3 wherein:
   (a) said gradient includes acetonitrile from below approximately 3% to at least approximately 5%, and
   (b) said selected and collected effluent-fractions are those having a refractive index between approximately 1.347 and approximately 1.353
whereby an amplifier material herein designated "Material Eta" is extracted in purified form.

8. The process of claim 1 wherein the following additional steps are included after said step (4):

(5) selecting predetermined effluent-fractions of said step (4);

(6) applying said effluent fractions of step (5) to a reverse-phase high-pressure liquid chromatography column packed with octadecylsilane;

(7) eluting said column with a pH-adjusted acetonitrile-in-aqueous-trifluoroacetic-acid-solution gradient, thereby producing a plurality of effluent-fractions; and (8) selecting predetermined fractions of step (7), and collecting them.

9. The process of claim 8 wherein said solution of said step (7) is approximately 0.1% (v/v), the pH thereof is adjusted to approximately 2.5, and the acetonitrile concentration of said gradient includes the range from approximately 0% to approximately 25%.

10. The process of claim 9 wherein:
(a) said fractions of steps (5) and (6) are Material Beta,
(b) said gradient includes acetonitrile from below approximately 11% to at least approximately 15%, and
(c) said selected and collected effluent-fractions of step (8) are those wherein the acetonitrile concentration is between approximately 11.8% and approximately 14.8% whereby the "Material Beta" of claim 4 is further purified and extracted in a substantially purified form, substantially free of extraneous material, said substantially purified material being herein designated "Amplifier Beta."

11. The process of claim 9 wherein:
(a) said fractions of steps (5) and (6) are Material Eta,
(b) said gradient includes acetonitrile from below approximately 14% to at least approximately 17%, and
(c) said selected and collected effluent-fractions of step (8) are those wherein the acetonitrile concentration is between approximately 14.8% and approximately 16.8% whereby the "Material Eta" of claim 7 is further purified and extracted in a substantially purified form, substantially free of extraneous material, said substantially purified material being herein designated "Amplifier Eta."

12. The process of claim 9 wherein:
(a) said fractions of steps (5) and (6) are Material Zeta,
(b) said gradient includes acetonitrile from below approximately 11% to at least approximately 16%, and
(c) said selected and collected effluent-fractions of step (8) are those wherein the acetonitrile concentration is between approximately 11.8% and approximately 15.8% whereby the "Material Zeta" of claim 6 is further fractionated and an amplifier herein designated "Amplifier Zeta-2" is extracted in a substantially purified form, substantially free of extraneous material.

13. The process of claim 1 wherein the following additional steps immediately follow said step (1) and immediately precede said step (2):

(1a) fractionating said dialysate by gel filtration, thereby producing a plurality of dialysate-fractions;

(1b) assaying said dialysate-fractions, by measuring fluram-reactivity; and (1c) selecting dialysate-fractions having substantial fluram-reactivity and pooling them for application to said column of said step (2).

14. The process of claim 13 wherein said aqueous-phosphate solution is approximately 0.02 M phosphate, the pH thereof is adjusted to approximately 5, and the acetonitrile concentration of said gradient includes the range from approximately above 0% to approximately 15%.

15. The process of claim 13 wherein said aqueous-phosphate solution is approximately 0.02 M phosphate, the pH thereof is adjusted to approximately 2.5, and the acetonitrile concentration of said gradient includes the range from approximately above 0% to approximately 20%.

16. The process of claim 15 wherein:
(a) said gradient includes acetonitrile from below approximately 12% to at least approximately 14%, and
(b) said selected and collected effluent-fractions are those wherein the acetonitrile concentration is between approximately 12.0% and approximately 13.5% whereby an amplifier material herein designated "Material Pi" is extracted in purified form.

17. The process of claim 15 wherein:
(a) said gradient includes acetonitrile from below approximately 14% to at least approximately 15%, and
(b) said selected and collected effluent-fractions are those wherein the acetonitrile concentration is between approximately 14.0% and approximately 14.5% whereby an amplifier material herein designated "Material Sigma" is extracted in purified form.

18. The process of claim 15 wherein:
(a) said gradient includes acetonitrile from below approximately 15% to at least approximately 17%, and
(b) said selected and collected effluent-fractions are those wherein the acetonitrile concentration is between approximately 15.8% and approximately 16.0% whereby an amplifier material herein designated "Material Upsilon" is extracted in purified form.

* * * * *